United States Patent
Palzer et al.

(10) Patent No.: US 10,762,348 B2
(45) Date of Patent: Sep. 1, 2020

(54) METHOD AND APPARATUS FOR DETERMINING THE POSITION AND/OR THE ORIENTATION OF AN EYE

(71) Applicant: PRECITEC OPTRONIK GMBH, Neu-Isenburg (DE)

(72) Inventors: Gabriel Palzer, Rodgau (DE); Christoph Dietz, Obertshausen (DE); Stefan Birmanns, Buch am Irchel (CH)

(73) Assignee: PRECITEC OPTRONIK GMBH, Neu-Isenburg (DE)

( * ) Notice: Subject to any disclaimer, the term of this patent is extended or adjusted under 35 U.S.C. 154(b) by 0 days.

(21) Appl. No.: 15/740,902

(22) PCT Filed: Jun. 28, 2016

(86) PCT No.: PCT/EP2016/064954
§ 371 (c)(1),
(2) Date: Dec. 29, 2017

(87) PCT Pub. No.: WO2017/001375
PCT Pub. Date: Jan. 5, 2017

(65) Prior Publication Data
US 2018/0189563 A1    Jul. 5, 2018

(30) Foreign Application Priority Data
Jun. 29, 2015   (DE) .................. 10 2015 008 217

(51) Int. Cl.
*G06K 9/00* (2006.01)
*A61B 3/14* (2006.01)
(Continued)

(52) U.S. Cl.
CPC .......... *G06K 9/00604* (2013.01); *A61B 3/107* (2013.01); *A61B 3/14* (2013.01);
(Continued)

(58) Field of Classification Search
CPC ........ G06K 9/00604; G06T 7/74; A61B 3/10; A61B 3/102; A61B 3/113; A61B 3/14;
(Continued)

(56) References Cited

U.S. PATENT DOCUMENTS 4,995,716 A * 2/1991 Warnicki ............... A61B 3/107
                                                              351/212
5,828,406 A * 10/1998 Parulski ............... H04N 1/0044
                                                              348/220.1
(Continued)

FOREIGN PATENT DOCUMENTS

| CN | 101726985 A | 6/2010 |
|----|-------------|--------|
| CN | 103917150 A | 7/2014 |

(Continued)

OTHER PUBLICATIONS

English Translation of Office Action of Chinese Application 201680028415.5 dated Jul. 2, 2019, 3 Pages.
(Continued)

*Primary Examiner* — Thai Q Tran
*Assistant Examiner* — Syed Y Hasan
(74) *Attorney, Agent, or Firm* — Lucas & Mercanti, LLP; Klaus P. Stoffel (57) ABSTRACT

A method for determining parameters for the position and orientation of the cornea of an eye and involves the steps of generating linear structures on the iris and/or sclera of the eye, having a camera capture a first image of the eye including the linear structures, and determining, on the basis of the first image, a distance and an orientation of the linear structures in relation to the camera.

20 Claims, 7 Drawing Sheets

(51) Int. Cl.
*A61B 3/107* (2006.01)
*G06T 7/70* (2017.01)
*G06T 7/73* (2017.01)

(52) U.S. Cl.
CPC ............... *G06T 7/74* (2017.01); *A61B 3/145* (2013.01); *G06T 2207/20061* (2013.01); *G06T 2207/30201* (2013.01)

(58) Field of Classification Search
CPC ........ A61B 3/152; A61B 3/107; H04N 5/225; H04N 5/23245
USPC .......... 348/78, 220.1, 333.11; 351/205, 206, 351/208, 210, 212, 209; 600/407, 427
See application file for complete search history.

(56) References Cited

U.S. PATENT DOCUMENTS

| | | | |
|---|---|---|---|
| 7,284,858 B2* | 10/2007 | Bergner | A61B 3/1005 351/205 |
| 7,413,305 B2 | 8/2008 | Baumann | |
| 7,600,873 B2 | 10/2009 | Grundig | |
| 2004/0008259 A1 | 1/2004 | Gokturk et al. | |
| 2010/0045933 A1* | 2/2010 | Eberl | A61B 3/113 351/210 |
| 2010/0103379 A1 | 4/2010 | Fiess | |
| 2013/0120712 A1* | 5/2013 | Spasovski | A61B 3/113 351/209 |
| 2014/0232988 A1 | 8/2014 | Kersting | |
| 2015/0018674 A1* | 1/2015 | Scott | A61F 9/00827 600/427 |
| 2016/0183787 A1 | 6/2016 | Lipari | |

FOREIGN PATENT DOCUMENTS

| | | |
|---|---|---|
| DE | 10250569 A1 | 5/2004 |
| DE | 102004052199 A2 | 4/2006 |
| DE | 102006002001 A1 | 7/2007 |
| DE | 102010024407 A1 | 12/2011 |
| WO | 2015011692 A1 | 1/2015 |

OTHER PUBLICATIONS

German Office Action, Application No. 10 2015 008 217.5 dated Feb. 16, 2016, 4 Pages.

Chen, Wenjing; Su, Xianyu: A New method for improving the measuring precision of 3D shapes. In: International Topical Symposium on Advanced Optical Manufacturing and Testing Technology. International Society for Optics and Photonics, Proc. of SPIE, vol. 4231, 2000, S. 412-415.

* cited by examiner

METHOD AND APPARATUS FOR DETERMINING THE POSITION AND/OR THE ORIENTATION OF AN EYE

The present application is a 371 of International application PCT/EP2016/064954, filed Jun. 28, 2016, which claims priority of DE 10 2015 008 217.5, filed Jun. 29, 2015, the priority of these applications is hereby claimed and these applications are incorporated herein by reference.

BACKGROUND OF THE INVENTION

The invention relates to a method and an apparatus for determining the position and the orientation of an eye.

Figure 2:
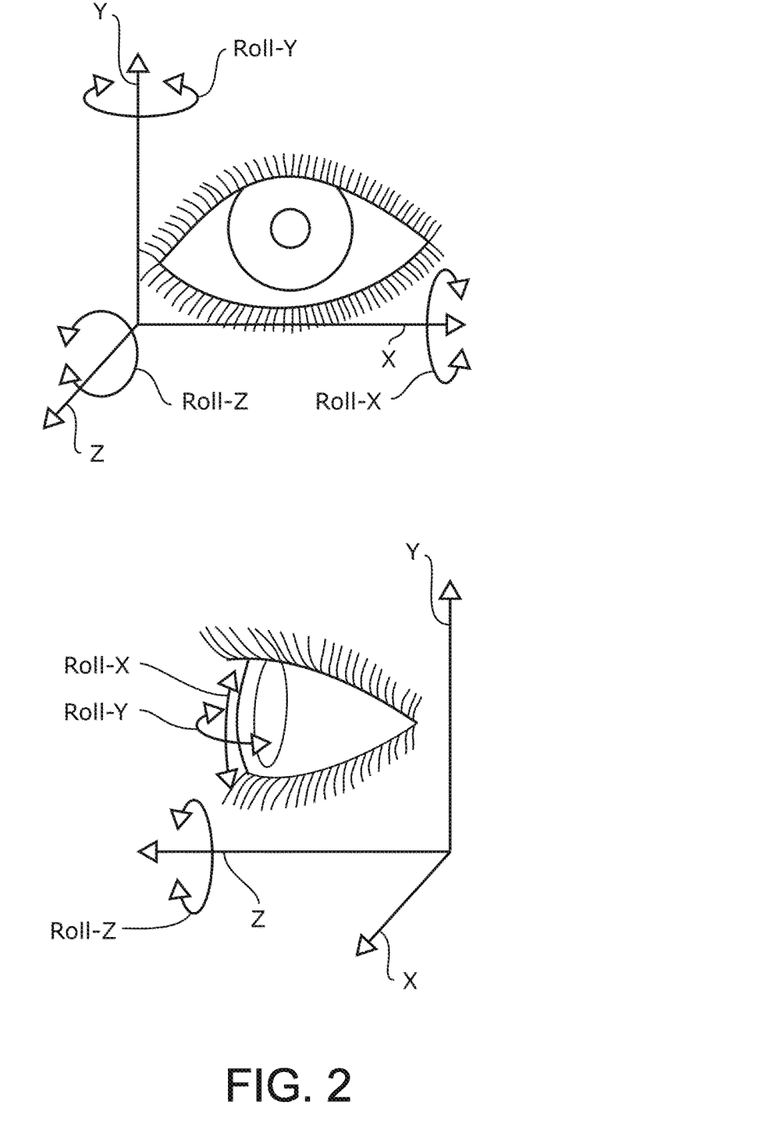
FIG. 2 shows coordinate and angle definitions in a schematic diagram.

Such methods and apparatuses are used in particular during refractive eye surgery, wherein the total refractive power of the eye can be altered and conventional optical corrections such as spectacles or contact lenses can ideally be obviated thereafter. Particularly during laser ablation for changing the corneal curvature, wherein generally an ablation laser beam is guided over the curved surface of the cornea, during the treatment it is necessary to know the exact position of the eye and also the orientation of the eye—that is to say the orientation of the eye with respect to three angles in space. The position of the eyeball in a Cartesian coordinate system with the coordinates X, Y and Z and also the orientation of the eyeball in relation to three spatial angles $Roll_x$, $Roll_y$ and $Roll_z$ are defined as follows in accordance with FIG. 2:

The Cartesian coordinates X, Y and Z are chosen such that the Z-axis substantially coincides with a laser processing axis A3 and is oriented in the viewing direction. The X-axis is oriented such that the X-axis coincides with the horizontal when a person is standing upright. Correspondingly, the Y-axis is arranged vertically. The spatial or rotation angles of the eyeball are defined in a manner corresponding to the Cartesian coordinates as roll angles $Roll_x$, $Roll_y$ and $Roll_z$. The angle $Roll_z$ is also called cyclotorsion.

One option for capturing the position and orientation of the eye consists in recording a camera image of the surface of the eye. The evaluation of the camera image has to take account of all possible movements of the eye during such an operation.

SUMMARY OF THE INVENTION

The invention is based on the object of specifying a method and an apparatus which make it possible to ascertain variables for determining the position and the orientation of the cornea of an eye with a sufficient accuracy for carrying out a laser-aided treatment of the cornea.

The method according to the invention comprises the following steps: linear structures are generated on the iris of the eye, for example by projection. A first image of the eye with the linear structures situated thereon is recorded by means of a camera. In this case, preferably the camera axis of the camera is aligned with the eye. Here and hereinafter, the camera axis is understood to mean the optical axis of the camera. A distance, that is to say a Z-coordinate, and parameters characterizing the orientation of the linear structures relative to the camera, such as $Roll_x$ and $Roll_y$, for example, are determined by means of the first image. From these indications it is then possible to deduce the distance and the corresponding parameters for an orientation of the surface onto which the structures are projected—that is to say the iris, for example. The distance and the corresponding parameters for the orientation of the cornea can in turn be determined therefrom. In this case, the parameters for a characterization of the orientation of the linear structures need not completely characterize the orientation.

The term linear structures is understood to mean for example straight lines, straight line segments, stripes, circle arcs, circles, ellipses, etc.—that is to say structures which can be represented by lines. The lines need not necessarily be straight lines, but rather can be curved or else closed as in the case of ellipses or circles. Preferably, the linear structures are situated on the iris. When determining parameters for the position and the orientation of the linear structures, it is possible to use for example the center of the linear structures or the edge between bright and dark. The orientation of the linear structures relative to the camera should be understood to mean an angle-dependent orientation of the linear structures in space. The orientation can be defined for example by the indication of two angle variables. The orientation of the eye in space can be deduced from the orientation of the linear structures. In particular, the angle variables required for completely indicating the orientation of the eye can be ascertained from the orientation of the linear structures. The lateral position is understood to mean the position of the eye perpendicular to the camera axis or a laser axis.

In order to ascertain variables which are necessary for example for carrying out a laser ablation of the cornea, namely the orientation of the eye and Z-position thereof, the method according to the invention takes as reference the iris of the eye rather than the actual cornea. On the iris, linear structures are projected and features are thus generated, which can be detected more easily than natural structures by means of image processing. The structures thus generated form a distinct contrast, which can thus be detected better and which simplifies image processing and yields more precise results from the image processing. At the same time, on account of their known geometry that varies to a lesser extent, the linear structures can be handled more easily than natural structures in the image processing.

In one development of the invention, provision can be made for a second image of the eye without linear structures situated thereon to be recorded by means of a camera and for a lateral position, that is to say the parameters X and Y, and/or a cyclotorsion of the eye, that is to say $Roll_z$, to be determined by means of the second image. Alternatively or additionally, the cyclotorsion can be determined by means of a third image. The cyclotorsion indicates a rotation of the eye about the camera axis or a laser axis. The recording of the second image and/or of the third image can be carried out by the same camera by which the first image is recorded. These supplementary steps enable a complete determination of the position and the orientation of an eye in a simple manner. The second and/or third image can be recorded at suitable points in time for example in the context of a measurement cycle. Such a measurement cycle can provide for example an initial recording of a first image with linear structures, an n-fold recording of further second images without linear structures and thereafter a recording of a third image. The third image can be recorded for example with a higher resolution than the second images. The values for Z and $Roll_x$ and $Roll_y$ can be determined from the first image. New values for X and Y and thus also for $Roll_x$ and $Roll_y$ can be determined from the second images. $Roll_z$ can be determined from the third image.

One preferred embodiment provides for determining the orientation of the linear structures to comprise determining a first tilt angle and a second tilt angle of the linear structures, in particular about axes perpendicular to the camera axis. A first and a second tilt angle can be determined particularly reliably on account of the projected linear structures. The image or camera axis can serve as a reference variable for the tilt angles. The orientation of the iris and thus also the orientation of the eye can be deduced on the basis of the tilt angles of the linear structures.

In one embodiment of the method, parameters characterizing the linear structures can be ascertained in order to determine the distance and the orientation. The parameters can be for example the position and the angle of the linear structures if the linear structures represent straight lines or stripes. A position of the midpoint and a radius could be involved, for example, in the case of circular or circle-arc-shaped structures.

Preferably, determining the distance and the orientation of the linear structures comprises applying a Hough transformation. A Hough transformation is advantageous in the case of linear structures which are describable by straight lines or circles. By means of the Hough transformation, from a multiplicity of linear structures ascertained, it is possible particularly advantageously to select the structures closest to the structures actually present.

Alternatively, in the method according to the invention, provision can be made for determining the distance and the orientation of the linear structures to comprise applying a one-dimensional Fourier transformation. In particular, characterizing parameters ascertained by means of the one-dimensional Fourier transformation can comprise a period along a direction and also a phase. The method of Fourier transformation is economic in its application and yields reliable results.

Advantageously, determining the distance and the orientation comprises determining, in the first image, a position of the totality of the linear structures, a distance between the linear structures and/or an angle of the totality of the linear structures. The position of the totality of the linear structures is understood to mean a geometric centroid of all captured linear structures or the position of a specific linear structure, from which the position of the rest of the linear structures can be derived. From the position of the totality of the linear structures in the first image, it is possible to draw conclusions about the distance between the linear structures and the camera and thus also about the distance of the iris and ultimately about the distance of the cornea from the camera. From the distance between individual linear structures or from an average distance between all the linear structures, it is possible to deduce a tilt of the linear structures in relation to the camera. The same applies to a variation of the angles of individual linear structures or of the angle of the totality of the linear structures. Similar conclusions can be drawn from a position of the midpoints and also an ellipticity or from a variation of same.

One advantageous embodiment provides for determining the distance and the orientation to comprise inserting geometric figures into the first image on the basis of the parameters ascertained. The basis of the geometric figures can be the ascertained parameters relating to the original linear structures. Advantageously, before the insertion the parameters ascertained are varied. The variation of the parameters can be for example a displacement of the geometric figures representing the original linear structures, a variation of the angles of individual or all geometric figures with respect to one another or/and a distortion of the geometric figures. While the linear structures are represented by individual pixels in the first image recorded by the camera, the variation of the parameters ascertained before the geometric figures are inserted makes it possible for example to carry out a displacement on a subpixel scale. After the subsequent insertion of the geometric figures ascertained, the process of determining for example the distance and the orientation of the linear structures can be carried out again. In this iterative process, a significant improvement in the result of the determination can be achieved depending on the quality, resolution and/or contrast of the first image.

In one embodiment, the step of determining the cyclotorsion and/or the position of the eye can comprise recording a reference image. On the basis of the reference image, by means of comparison with the second image currently recorded, it is possible to capture a rotation of the eye about the camera axis or laser axis and a variation of the position of the eye, for example of the pupillary midpoint.

One embodiment provides for outputting the position or/and the orientation of the cornea of the eye. The output forms the interface to a control device that defines the position for example of a laser for the ablation of the cornea.

The apparatus according to the invention for determining variables for the position and the orientation of the cornea of an eye comprises a projector for generating linear structures on the iris of the eye, a camera, the camera axis of which is aligned with the eye, and also a control device, which is connected to the projector and the camera. The control device is configured to record a first image of the eye with the linear structures by means of the camera, and to determine, on the basis of the first image, a distance and an orientation of the linear structures relative to the camera. The advantages of the method already described are achievable by means of this apparatus.

In one advantageous development, the apparatus can be configured to record a second image of the eye without linear structures by means of the camera, and to determine, on the basis of the second image, a cyclotorsion of the eye and a lateral position of the eye.

In one advantageous configuration, the control device can be configured, for the recording of the second image, to read out the second line of the camera, or/and to combine two pixels into one pixel. Consequently, the same camera can be used for two different operating modes in order to achieve higher image repetition rates and/or lower latencies.

Furthermore, it can be advantageous if an illumination device is provided, which is configured to at least partly illuminate the cornea for the recording of the second image. Particularly for the purpose of increasing the contrast during the recording of the second image, it can be advantageous to brighten the iris and its surroundings and to illuminate the eye in a planar manner.

BRIEF DESCRIPTION OF THE DRAWING

The invention will now be explained in greater detail with reference to the drawings, in which.

DETAILED DESCRIPTION OF THE INVENTION

Figure 1:
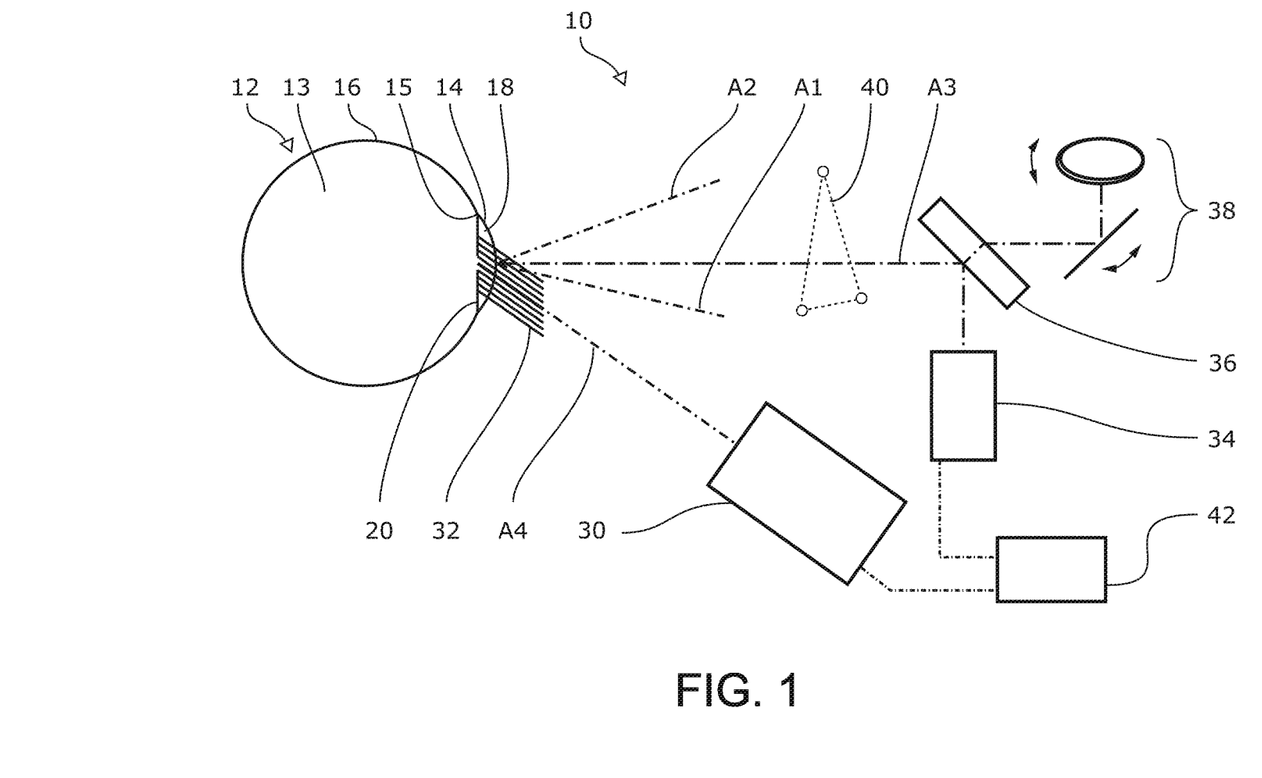
FIG. 1 shows a schematic diagram with an apparatus for the laser treatment of the cornea of an eye.

FIG. 1 schematically shows the construction of a system 10 for the laser treatment of an eye 12 of a patient. Of the eye 12 there are shown in FIG. 1 the eyeball 13, also called bulbus oculi, with the outer cornea 14, adjoined by the sclera 16 in the circumferential direction of the cornea 14. Situated behind the cornea 14 further inward in the radial direction is the anterior chamber 18 of the eye, extending from the cornea 14 to the iris 20. The iris 20 separates the anterior chamber 18 of the eye from the posterior chamber of the eye. The boundary region between cornea 14 and sclera 16 is called the limbus 15. The outer circumference of the iris 20 is situated at the limbus 15. The inner circumference of the iris 20 forms the pupil 22. This is illustrated in greater detail in FIG. 3.

Figure 3:
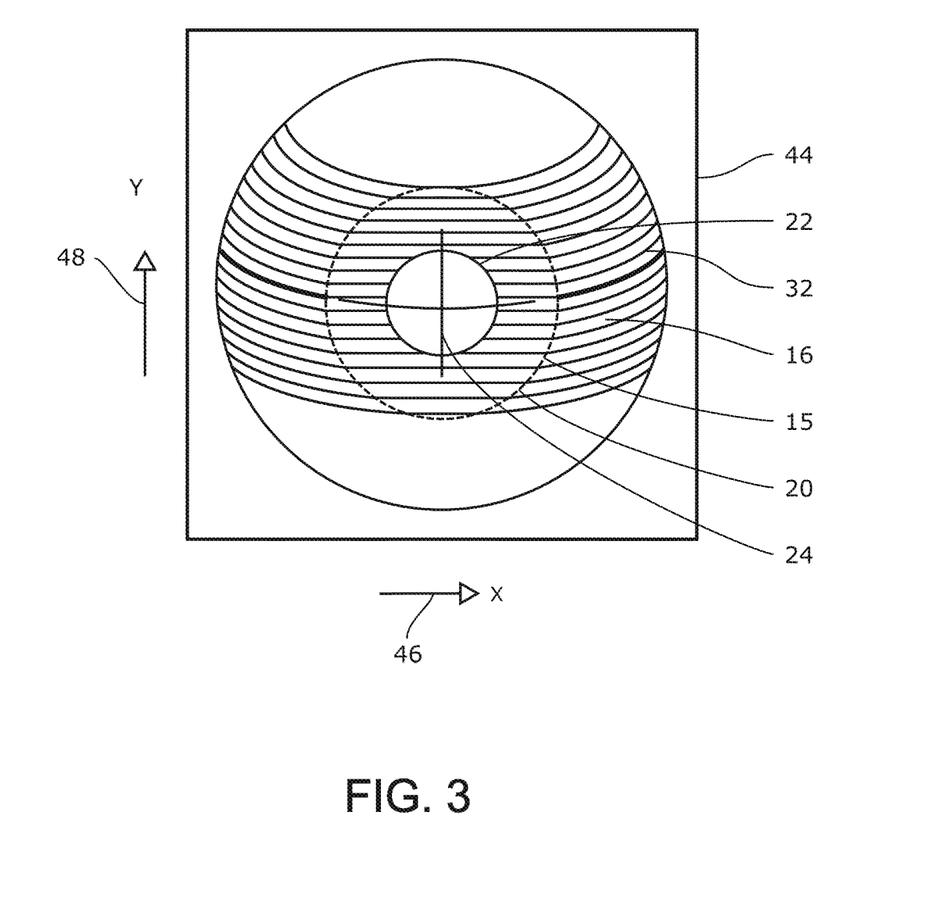
FIG. 3 shows an image from the camera of the apparatus from FIG. 1 with projected linear structures.

The apparatus 10 comprises a projector 30 for projecting a stripe pattern 32 on the iris 20 of the eye 12, a camera 34, which is aligned with the iris 20 of the eye 12 frontally via a beam splitter 36, and also a laser beam scanner 38 comprising a galvo-mirror array, via which scanner a laser beam suitable for the ablation of the cornea 14 can be guided over the cornea 14. Provision is made for projecting a line or a crosshair onto the cornea 14 via two different projection axes A1, A2. Such a crosshair 24 is illustrated in FIG. 3. An illumination by means of three luminous points 40 is furthermore provided. The luminous points illuminate the cornea 14 or the iris 20 and enable a contrast enhancement during the recording of camera images. Besides the constituent parts mentioned, the system comprises a mount for positioning the patient's head, a fixation laser as an aid for positioning the head and the cornea, which are not illustrated in FIG. 1. FIG. 1 additionally shows a control device 42, which is designed for driving and for recording, processing and forwarding of data of at least the camera 34 and of the projector 30.

The position of the eyeball 13 in a Cartesian coordinate system with the coordinates X, Y and Z and also the orientation of the eyeball 13 in relation to three spatial angles $Roll_x$, $Roll_y$ and $Roll_z$ are defined in accordance with FIG. 2 as already described above.

Some preparatory activities should be carried out before the use of the system 10. A calibration of camera 34 and projector 30 with respect to one another should be performed, that is to say that a relative positioning of camera 34 and projector 30 is ascertained. To that end, instead of the eye 12 a calibration body is positioned and the stripe pattern 32 is projected onto the calibration body. The calibration body can for example be an area having a size of 25 mm by 45 mm and having a 3 mm high step in the center and have a white and planar light-scattering surface. Such a calibration body reproduces the optical properties of the eye 12, in particular of the cornea 14 and of the sclera 16, for the present application. The image of the stripe pattern 32 situated on the calibration body, said image being recorded by the camera 34, can then be calibrated to the actual size and the actual distance of the stripe pattern 32 from the camera 34. For the correct sequence of the laser treatment, the positioning of the ablation laser has to be checked. For this purpose, the laser scanner 38 is calibrated, for example by a square with a size of 10 mm by 10 mm being shot on a suitable material. The actual length and the actual width of the geometric figure are entered into the control device 42, for example, and a suitable correction value is calculated. A distortion that may possibly occur is not taken into account here.

For the alignment of the accurate position of the laser processing axis A3 relative to the camera 34, a photographic paper at the position of the calibration body or of the eye 12 is bombarded before the treatment with the ablation laser. The position of the structures generated on the photographic paper can be coordinated with the position of the structures in the image from the camera 34 and, if appropriate, a correction value can be ascertained.

Upon carrying out the calibration processes mentioned, the relative position of camera 34 and projector 30 is known. In particular, upon the recording of the calibration body by the camera 34, an image is present whose visible structures are known exactly in particular with regard to their dimensions and orientation.

Besides the calibration of the overall system 10 that is carried out in this way, the depth of the anterior chamber 18 of the eye has to be measured by diagnosis systems and fed as a parameter to the system 10. The average magnitude for the depth of the anterior chamber is 3.0 mm. This magnitude represents a reference between the iris 20 and the cornea 14.

In preparation for the treatment, the patient's head and in particular the eye 12 to be treated are disposed within the apparatus 10. Firstly, the patient is asked to fixate a fixation laser coupled in via the optical axis of the laser processing axis A3. This ensures that the eye 12 is aligned with the minimum angular deviation from the ideal alignment along the optical axis A3. By means of the line or crosshair radiated in via the projection axes A1 and A2, the treating physician is enabled to achieve the best possible lateral positioning of the eye 12 with respect to the optical axis A3 by virtue of the overlap of the two features on the cornea 14. Furthermore, the treating physician visually monitors whether the pupil 22 and the eyeball 13 are situated as centrally as possible with respect to the patient's head.

At the beginning of the treatment, a reference image is recorded by means of the camera 34, said reference image serving for ascertaining the cyclotorsion and a lateral position of the eye 12 with respect to the optical axis A3. An image of the iris 20 without the projected stripe pattern 32 is recorded in this case.

In the further course of the treatment, the control device 42 ascertains a $Roll_x$ value, a $Roll_y$ value and a Z value from the stripe pattern 32 projected onto the iris 20 and outputs corresponding correction values for the laser scanner 38. This can also already be carried out for the first laser shot. In order to ascertain the cyclotorsion and a lateral position of the eye with respect to the laser processing axis A3, a camera image without projected stripes is recorded. If the X, Y or Z values ascertained lie outside a permissible range of values, the treatment is interrupted. The evaluation of the two images mentioned will be discussed in detail below.

FIG. 3 shows an image recorded by the camera 34 of the apparatus 10 with the projected stripe pattern 32 on the surface of the iris 20.

From the position of the center of the pupil 22 in the camera image it is not possible to ascertain unambiguously whether the position of the pupil 22 is caused by a translation of the eyeball 13 or by a rotation, also called roll movement, of the eyeball 13. In this regard, by way of example, a roll angle $Roll_y$ of 5.7° of the iris 20, given an anterior chamber depth z1 of 3.0 mm, may correspond to a lateral offset dx of 0.3 mm of the cornea 14 with respect to the pupil 22:

$$\tan(\text{Roll}_y) = \tan(5.7°) = 0.1$$

$$dx = z1\ \tan(\text{Roll}_y) = 0.3\ \text{mm}$$

This simplified consideration does not take account of image distortions as a result of the curvature or a difference in refractive index of the cornea 14. Since, for a positionally accurate laser treatment, the lateral position of the cornea 14 ought to be known accurately to 0.05 mm, a tracking of the ablation laser beam by the laser scanner 38 during the treatment is indispensable. During such a treatment, a patient's head moves laterally involuntarily by ±5 mm. The eyeball 13 varies its roll angle alignment, even with a gaze kept deliberately fixed, by ±3° on account of involuntary eye movements and short saccades.

Besides ascertaining the lateral position of the cornea 14, it is also necessary to determine the exact Z-position of the cornea 14. The Z-position cannot be ascertained with sufficient accuracy, solely from the diameter of the iris 20 or a scale of structures that are discernible on the iris 20. For a positionally accurate laser treatment, the Z-position of the cornea 14 should be known accurately to ±0.25 mm since the laser beam that performs the ablation is focused onto the surface of the cornea 14 and an incorrect depth of focus has disadvantageous effects on the treatment result. In order to minimize a movement of the eye 12 in the Z-direction, the patient's head is placed on a hard support. Further effects which result in a movement of the cornea 14 in the Z-direction, but are disregarded, are an eyeball diameter that is variable by approximately ±0.03 mm synchronously with the heart beat and also muscular movements that deform the cornea 14 depending on the focusing state of the eye lens and the opening state of the pupil 22. A maintenance of the Z-position of the cornea 14 within a tolerance window is monitored during the treatment. If the tolerance window is transgressed, the treatment is terminated and a renewed focusing procedure has to be carried out.

Firstly, a description will be given of the procedure for ascertaining the angle coordinates $\text{Roll}_x$ and $\text{Roll}_y$, and also the Z-coordinate:

The $\text{Roll}_x$, $\text{Roll}_y$, and Z-position values are ascertained on the basis of an image from the camera 34, in which at least the iris 20 exhibits the projected stripe pattern 32. In this case, every N-th, for example every thirty-second, image from the camera 34 is evaluated by the control device 42 of the system 10. In this recorded first image, an equation of a straight line is established individually for each stripe of the stripe pattern 32. Each individual stripe is able to be captured in an individualized manner. This can be done for example by a central stripe being marked as it were, for example by means of a larger width—as is illustrated for example in FIG. 3—or for example by means of a structuring of a selected stripe.

Prior to ascertaining the straight lines in the first image, it is possible for the image to be preprocessed. For this purpose, the camera image is improved by filter operations such that lines stand out clearly against the background. For this purpose, a correlation with a line original, also called line template, is carried out in one image direction, for example in a horizontal image direction. The line template shows synthetic lines, that is to say lines generated in the image, in the region of the iris. The course of the linear structures may be evident for example from an image of the calibration body. The line template thus represents a previously ascertained image—for example generated from calculations or recorded at a calibration body—which reproduces lines that possibly occur. In the case of deviating Z, $\text{Roll}_x$ and/or $\text{Roll}_y$ parameters, the course of the linear structures can be determined from a geometric model of the imaging optical units such as, for example, the object and image distances and also the triangulation angle. The template may be determined for example in a previous calibration for a specific projector. A correlation with the line template amplifies in each line pixels that might belong to a line on account of their own intensity and that of their neighbors. At the same time, thermal noise possibly present in the camera sensor or disturbing structures in the iris are attenuated by this correlation filtering. A comparable filter operation is carried out in a further image direction, for example in the vertical direction. Here, too, pixels that might belong to a uniform pattern such as a line, for instance, are highlighted.

In a further step, a so-called skeletonization can be carried out, which involves for example removing the outer pixels of a line step by step in order to obtain a line having the width of one pixel. After these preprocessing steps, the linear structures, that is to say for example straight lines or circles, stand out as strokes one pixel wide in the image.

In order to ascertain the equations of straight lines, two alternative methods are applied. In order to ascertain parameters that mathematically reproduce the linear structures, as a first possible alternative a Hough transformation is applied to the image. In this case, the optionally preprocessed camera image is transformed into a space that assesses each pixel with regard to the association thereof with a linear structure. In the Hough transformation, line objects in the form of straight lines in the two-dimensional camera image are characterized by a distance vector r with respect to the image midpoint and a straight line gradient, for example an angle with respect to the X-axis, and transferred in accordance with their weighting as grayscale value to a pixel having the coordinates (r, α) in the two-dimensional Hough space. A similar situation is also applicable, of course, to circular objects; a possibly elliptically distorted circle may involve for example the coordinates of the midpoint and the lengths of ellipse axes. Each pixel of the preprocessed camera image is checked with regard to its association with a linear structure and forms in the Hough space a point whose coordinates are dependent on its association with a linear structure. On the basis of the pixel structure of the preprocessed camera image, a corresponding matrix structure, also called voting matrix, arises in the Hough space. In this matrix, the linear structures are discernible on the basis of an accumulation of points in the matrix.

The assessment of the structures ascertained may involve performing a weighting of the individual linear structures or parts thereof. By way of example, stripes at the outer edge of the iris 20—near the boundary with respect to the sclera 16—may be weighted particularly heavily. Since the iris 20 is surrounded by the aqueous humor in the anterior chamber and is not a rigid structure, the Z-position of the iris 20 may fluctuate at the pupil edge 22—a fluctuation by up to 1 mm may arise depending on lens accommodation and pupil opening during the treatment. It has been found that the iris has a smaller variation in the region of its outer circumference—near the suspensory point.

Besides the projected linear structures on the iris 20, it is also possible to evaluate those on the sclera 16 near the limbus 15, the boundary between white sclera 16 and colored iris 20. Furthermore, there is the possibility of deducing from the contour of the limbus 15—optionally without projected structures—the tilt thereof: a circular shape of the limbus 15 becomes an elliptic shape upon a rotation of the eyeball 13. In the preferred arrangement, however, the camera is directed frontally at the eye 12, such that there is only a slight change in the width of the limbus 15 proportionally to the cosine of the roll angle. By means of an inclined camera, it is possible to improve the sensitivity of this method in one dimension. It would then be necessary advantageously to provide two cameras aligned with the eyeball 13 obliquely from x- and y-directions.

Figure 4:
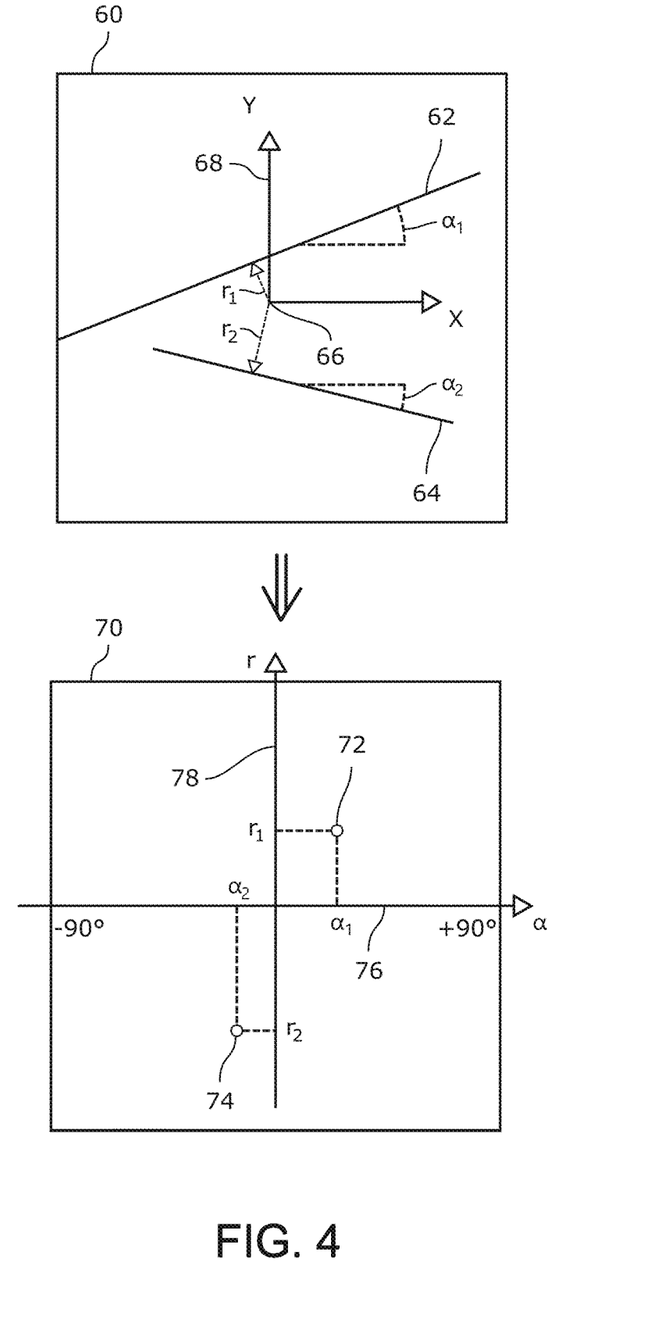
FIG. 4 shows a schematic illustration of a Hough transformation.

FIG. 4 illustrates the principle of a Hough transformation. A first diagram 60 shows two straight line segments 62, 64 in a Cartesian coordinate system. The straight lines 62, 64 are parameterized in accordance with the Hesse normal form, which includes a distance vector r from the origin 66 and also an angle α, here for example with the horizontal X-axis 66, running perpendicularly to the y-axis 68, running vertically in the diagram. The first straight line 62 is characterized by the parameter set $(r_1, \alpha_1)$, and the second straight line by the parameter set $(r_2, \alpha_2)$. By means of the Hough transformation, the straight lines 62, 64 are transformed into the Hough space and represented there as a first point $(r_1, \alpha_1)$ 72 and as a second point $(r_2, \alpha_2)$ 74. The Hough space is illustrated in the diagram 70 in FIG. 4. The angle α formed between a straight line and the X-axis 66 in the Cartesian coordinate system 60 is plotted on the abscissa 76. The ordinate 78 bears the signed distance information r. The more pixels from the Cartesian coordinate system 60 are assigned to a straight line in the Hough space and are thus plotted as a point in the diagram 70, the higher becomes the grayscale value of the point at the corresponding location in the Hough diagram 70.

The parameters thus ascertained of the linear structures, that is to say for example reference points and gradient angles in the case of straight lines, are then correlated with the actually projected stripe pattern 32. This is carried out with the aid of an original coordination in the Hough space. For this purpose, all stripe patterns whose position and orientation parameters appear plausible are ascertained as originals, also called templates, and transformed into the Hough space. These transformed originals are then correlated with the actually ascertained camera image, transformed into the Hough space. High correlation values arise at locations at which the Hough space original has a linear structure, which are also present in the camera image transformed into the Hough space. The original having the highest correlation value is regarded as that stripe pattern 32 of the projection 34 on the iris 20 which is recorded by the camera 34. A position of all linear structures in the image, the distances between the linear structures and, if appropriate, angle or distortion values can be inferred from the original thus ascertained. The originals used for the original coordination may be for example a set of computer-generated Hough-transformed stripe originals.

In order to improve the accuracy of the position parameters of the linear structures in the camera image, it is possible to perform a back projection of the parameterized linear structures into the camera image. For this purpose, the ascertained parameterized linear pattern is displaced and/or distorted in subpixel steps within the camera image and the resultant image is subsequently correlated with the original camera image. In this method which improves the accuracy of the position of the linear structures in the image, it is possible to use an optimization method, such as the gradient method, for example, since the search space in the image is without pixel rasterization and thus correspondingly large.

The tilt of the iris 20, assumed to be planar, can be ascertained from the parameterized linear objects thus ascertained: if the linear objects are straight lines, the $\text{Roll}_x$ and $\text{Roll}_y$ angles can be determined from the distances between the straight lines and from the gradient of the straight lines.

The Z-distance between the plane of the iris 20 and the camera 34 can be ascertained from the position of the straight lines in the camera image.

Figure 5:
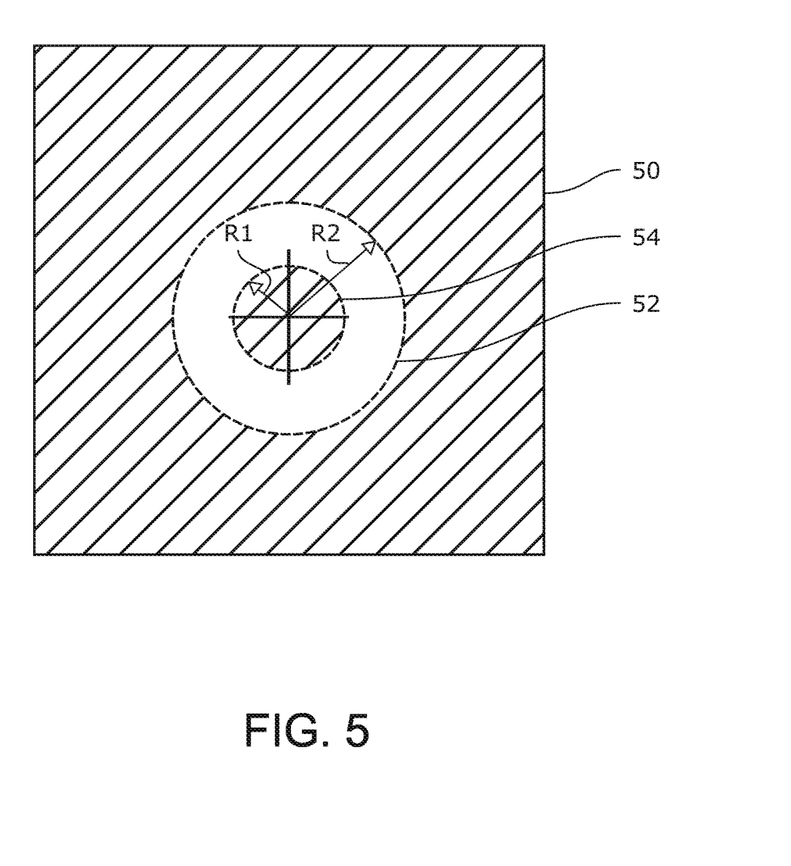
FIG. 5 shows a mask for the evaluation of the image from FIG. 3.

A mask can be used in order to ascertain more easily the linear objects lying in the image from the camera 34. Such a mask is shown in FIG. 5. The mask masks out all image contents around the iris 20 and within the pupil 22. Two circle arcs with the radius R1 for the diameter of the pupil 22 and R2 with the outer radius of the iris 20 are defined for this purpose.

Figure 6:
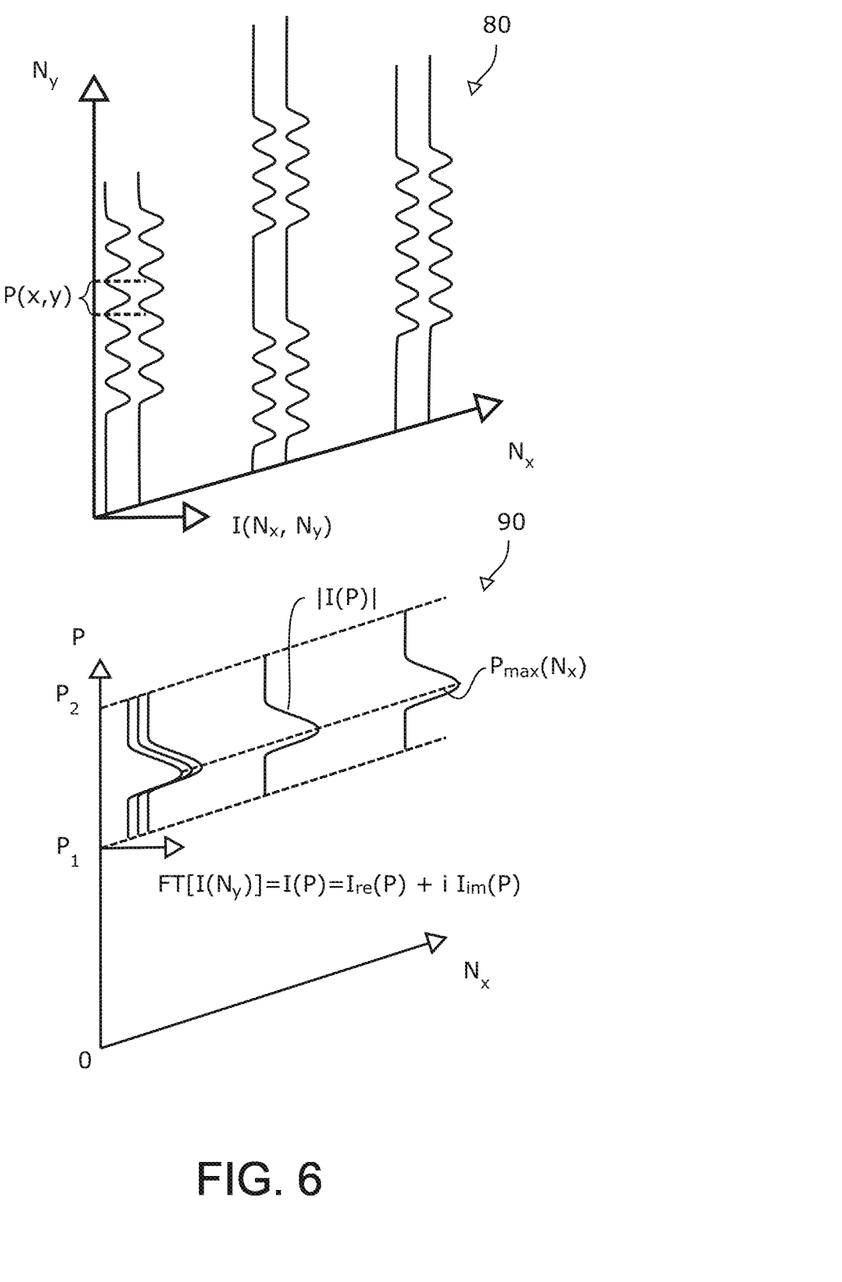
FIG. 6 shows a schematic illustration of a Fourier transformation.

As an alternative to an evaluation of the camera image by means of a Hough transformation, the evaluation of the stripe pattern 32 can be carried out using a one-dimensional Fourier transformation. Preferably, the distances between the lines of the stripe pattern are uniform or vary only slightly, in order to keep the quality of the Fourier transformation high. This is illustrated in the diagrams 80 and 90 in FIG. 6. Diagram 80 shows the image—recorded by the camera 34—of the iris 20 as an intensity distribution $I(N_x, N_y)$ of the individual pixels $(N_x/N_y)$ along a pixel column $N_x$. The individual stripes are represented as juxtaposed intensity peaks; in the center of the diagram, the pupil becomes apparent as lack of intensity. The tilt of the iris 20 is derived from the profile of period and orientation of the individual stripes of the projected stripe pattern 32 for example along the X-direction. For this purpose, the pixel intensity $I(N_x, N_y)$ for each X-pixel column is subjected to one-dimensional Fourier transformation:

$$I(P, N_x) = \sum_{N_y \text{ in mask}} I(N_x, N_y)\left(\cos\left(\frac{2\pi}{P}N_y\right) + i\sin\left(\frac{2\pi}{P}N_y\right)\right)$$

The mask, as shown in FIG. 5, can be used here as well. The Fourier transformation is carried out only for a few period values P in the value range P1 . . . P2 of the stripe period since the period value $P_{max}$ at which the maximum of the magnitude of the Fourier transform $I(P, N_x)$ lies is already known beforehand. It is therefore sufficient to calculate the Fourier transform for a few P-values around the maximum $P_{max}$. This is illustrated in diagram 90. The stripe period lies at the centroid of the magnitude $|I(P,N_x)|$ of the Fourier transform at $P=P_{max}$ and enables statements to be made about the distance between the projected straight lines. The angle $\text{Roll}_x$ is determined from the average value of $P_{max}$. Eye roll about an axis such as the x-axis, for example, leads to a change in the stripe period $P_{max}$ in the camera image. The phase φ of the complex-valued Fourier transform is determined at the point $P=P_{max}$:

$$\phi(N_x) = \arctan\left(\frac{\text{Im}(I)}{\text{Re}(I)}\right); I(P) \text{ at } P = P_{max}$$

The phase φ provides information about the Y-position of the stripe pattern 32 in the camera image. The Z-position of the iris 20 can be determined from the average Y-position of the stripe pattern 32. The second angle parameter $\text{Roll}_y$ can be ascertained from the gradient, i.e. the profile of the phase in the X-direction.

With both methods described—Hough transformation and Fourier transformation—it is possible to ascertain the tilt of the iris with respect to the angles $\text{Roll}_x$ and $\text{Roll}_y$ and also the offset of the iris along the Z-axis A3. The still missing variables of a lateral offset of the iris 20 and the cyclotorsion—$Roll_z$—are ascertained on the basis of a camera image without a projected stripe pattern 32. In this case, the camera image without projected stripes is compared with a reference image and a cyclotorsion, that is to say a rotation by the angle $Roll_z$, is ascertained on the basis of features of the iris 20. Furthermore, the edge of the pupil 22 is determined in order thus to obtain a diameter of the pupil 22 and the midpoint thereof. Additionally or alternatively, it is possible to ascertain the transition from the iris 20 to the white sclera 16, that is to say the limbus 15, in order to obtain a diameter and a midpoint here as well.

Two different recording modes may be used during the recording of the camera images by means of the camera 34. The camera 34 used in the present exemplary embodiment may be a CMOS camera, for example, and record images at a frequency of, for example, more than 1000 Hz, for instance 1200 Hz. For the recording of the iris with the projected stripe pattern 34, a specific resolution, for instance 512 times 512 pixels, is used, and only every N-th, for example every thirty-second, image is evaluated. By way of example, just half the resolution, for instance 256 times 256 pixels, may be used for the recording of the camera image without projected stripes. By way of example, only every second line of the camera 34 may be read out for this purpose. In addition, two pixels of a line may be combined into one pixel. In this way, only a quarter of all available pixels are captured, which significantly accelerates the evaluation.

Figure 7:
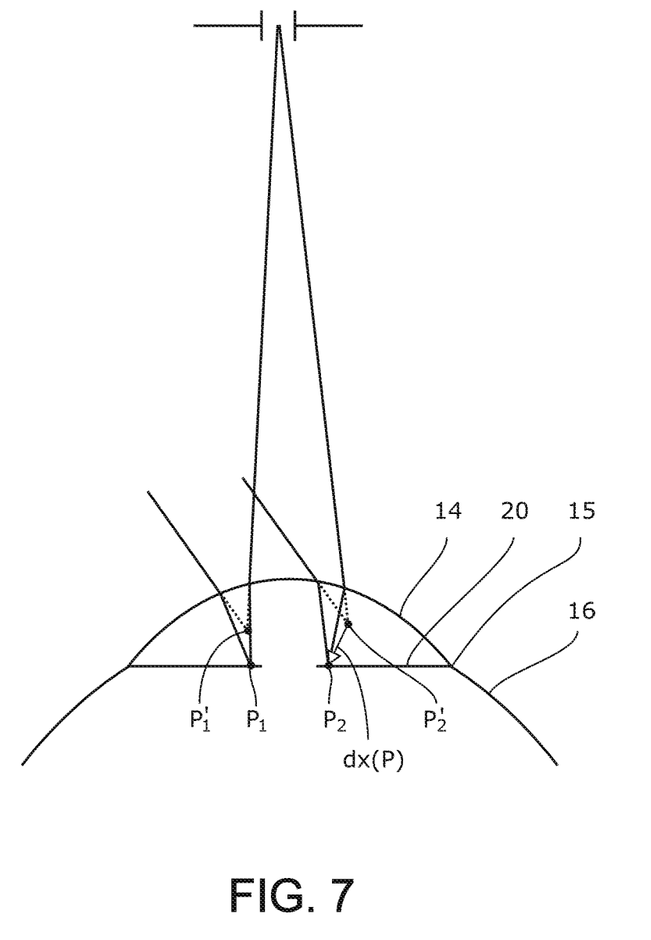
FIG. 7 shows an illustration of a possible correction of the data obtained from the image.

The position of the cornea 14 as coordinates X, Y is determined from the zero point of the iris 20 and a parallax of the position of the cornea 14 on account of the rotation of the eyeball 13 from the zero position. This parallax is calculated from the roll angles $Roll_x$, $Roll_y$ and the depth of the anterior chamber. This is illustrated in FIG. 7. In the simplest case, the light deflection by the curved cornea 14 is disregarded and the points $P_1'$, $P_2'$ result. Alternatively, it is possible to employ a method for correcting the systematic position errors resulting therefrom with a location-dependent 3D displacement vector dX(P), which is shown by way of example for the point $P_2$ in FIG. 7. In order to ascertain the displacement vector dx(P), it is possible to use either a computer-simulated ray tracing of the optical system or a calibration of the stripe projection with the camera system:

In the case of a computer-simulated ray tracing of the optical system, it is possible to compute a ray for example of a projected stripe as far as the iris 20. The optical system is formed by the cornea and the aqueous humor in the anterior chamber of an average eye. The iris 20 forms a light-scattering plane surface. Proceeding from the iris 20, it is possible to compute furthermore a ray as far as the aperture opening of the camera 34. From these calculations, dX(P) can be ascertained and used as a correction value for the (X, Y, Z)-position. In this case, the projection can be calibrated with a free-standing calibration body.

Alternatively, during the above-described calibration of the projection/camera system, by way of example, a planoconvex lens can be placed onto the calibration body. The planoconvex lens can be configured such that it simulates as well as possible the optical properties of an average eye such as radius of curvature, refractive index and/or distance to the iris. The displacement vector dx(P) can thus already be ascertained in the calibration and be contained in the calibration characteristic curve.

Overall, the following data are obtained from the two recorded camera images by means of the evaluation methods described above:

The orientation of the cornea 14 results from the roll angles $Roll_x$ and $Roll_y$, of the plane of the iris 20 such as were ascertained from the first camera image with the projected stripe pattern 32. The Z-coordinate of the cornea 14 is also determined from said first camera image. The angle $Roll_z$, that is to say the cyclotorsion, is determined from the second camera image without a projected stripe pattern 32. Said second camera image also reveals the position of the cornea 14 as Cartesian coordinates X, Y, corrected by means of the roll angles $Roll_x$, $Roll_y$ as described.

The invention claimed is:

1. A method for determining a position and an orientation of a cornea of an eye, comprising the steps of:
projecting linear structures directly on an iris of the eye;
recording a first image of the eye with the linear structures on the iris using a camera;
determining, using the linear structures on the iris of the eye of the first image, a distance and parameters characterizing the orientation of the linear structures relative to the camera, wherein the iris is assumed to be planar; and
determining the position and orientation of the cornea of the eye from the distance and parameters that characterize the orientation of the linear structures on the iris.

2. The method according to claim 1, further comprising the step of determining the distance and parameters characterizing the orientation of the cornea using the distance and parameters characterizing the orientation of the linear structures.

3. The method according to claim 1, wherein the step of determining parameters characterizing the orientation includes determining a first tilt angle and a second tilt angle of the linear structures about axes perpendicular to a camera axis.

4. The method according to claim 3, wherein the step of determining the distance and parameters characterizing the orientation includes applying a one-dimensional Fourier transformation, and the characterizing parameters comprise a period along a direction and also a phase.

5. The method according to claim 1,
wherein the step of determining the distance and parameters characterizing the orientation includes ascertaining parameters characterizing the linear structure.

6. The method according to claim 5, wherein the step of determining the distance and parameters characterizing orientation includes ascertaining the parameters of position and the angle of the linear structures.

7. The method according to claim 6, wherein the step of determining the distance and parameters characterizing orientation includes ascertaining the parameters Z, $Roll_x$ and $Roll_y$ of the linear structures.

8. The method according to claim 5, wherein determining the distance and parameters characterizing the orientation includes applying a Hough transformation.

9. The method according to claim 1, wherein the step of determining the distance and parameters characterizing the orientation includes determining, in the first image, a position of a totality of the linear structures, a distance between the linear structures and/or an angle of the totality of the linear structures.

10. The method according to claim 1, wherein the step of determining the distance and parameters characterizing the orientation includes inserting geometric figures into the first image based on the parameters ascertained, wherein before the insertion the parameters ascertained are varied on a subpixel scale.

11. The method according to claim 1, further comprising the following steps:

recording a second image of the eye without linear structures using a camera; and determining, using the second image, a lateral position and/or a cyclotorsion of the eye relative to the camera.

12. The method according to claim 11, wherein the step of determining the cyclotorsion and/or the lateral position of the eye includes recording a reference image.

13. The method according to claim 1, further comprising the step of outputting parameters characterizing the position or/and the orientation of the cornea of the eye.

14. The method according to claim 13, wherein the step of outputting parameters includes outputting the Z-position and also the $Roll_x$, and $Roll_y$ values.

15. The method according to claim 1, wherein the step of determining the distance and parameters characterizing the orientation includes weighting the linear structures at an outer edge of the iris at boundaries with respect to the sclera.

16. An apparatus for determining position and orientation of a cornea of an eye, comprising:
    a projector for projecting linear structures directly on the iris of the eye;
    a camera having an axis aligned with the eye; and
    a control device connected to the projector and the camera and configured to record a first image of the iris of the eye with the linear structures by way of the camera, the control device being configured to determine based on the linear structures on the iris of the eye of the first image, a distance and parameters characterizing the orientation of the linear structures relative to the camera, wherein the iris is assumed to be planar, and further configured to determine the position and orientation of the eye from the distance and parameters that characterize the orientation of the linear structures on the iris.

17. The apparatus according to claim 16, wherein the apparatus is configured
    to record a second image of the eye without linear structures by way of the camera, and
    to determine based on the second image, a cyclotorsion of the eye and/or a lateral position of the eye.

18. The apparatus according to claim 17, wherein the lateral position of the limbus is determined.

19. The apparatus according to claim 17, wherein the control device is configured, for the recording of the second image, to read out only every Nth line of the camera or/and to combine N pixels into one pixel.

20. The apparatus according to claim 17, further comprising an illumination device configured to at least partly illuminate the cornea for the recording of the second image.

* * * * *